United States Patent [19]

Kligerman

[11] Patent Number: 5,651,962
[45] Date of Patent: Jul. 29, 1997

[54] DRY PRE-SHAVING COMPOSITION

[76] Inventor: Myron R. Kligerman, 13468 Alberta Ave., Port Charlotte, Fla. 33981

[21] Appl. No.: 531,414

[22] Filed: Sep. 21, 1995

[51] Int. Cl.$^6$ ............................. A61K 7/06; A61K 7/15; A61K 9/14; A61K 9/12
[52] U.S. Cl. ..................... 424/73; 424/69; 424/401; 424/489; 424/43; 514/951
[58] Field of Search .................. 424/73, 69, 401, 424/489; 514/951

[56] References Cited

U.S. PATENT DOCUMENTS

| | | | |
|---|---|---|---|
| 2,390,473 | 12/1945 | Teichner | 206/56 |
| 2,548,891 | 4/1951 | Gantner | 167/92 |
| 3,429,964 | 2/1969 | Rieger | 424/73 |
| 4,457,912 | 7/1984 | Scodari | 424/73 |
| 4,933,177 | 6/1990 | Grollier et al. | 424/74 |
| 5,093,099 | 3/1992 | Haishi et al. | 423/622 |
| 5,165,915 | 11/1992 | Tokubo et al. | 424/63 |

*Primary Examiner*—Thurman K. Page
*Assistant Examiner*—James M. Spear
*Attorney, Agent, or Firm*—Frank A. Lukasik

[57] ABSTRACT

A pre-shave composition for an electric shaver consisting of a dry, finely ground blend of only three ingredients in definite, prescribed weight percentages, said ingredients being Kaolin, Zinc Oxide and Calcium Carbonate. A small amount of flesh tint and fragrance may optionally be added.

5 Claims, No Drawings

DRY PRE-SHAVING COMPOSITION

1. Field of the Invention

This invention pertains to a shaving composition to be used prior to shaving with an electric razor.

2. Background of the Invention

The art indicates that there are a number of cosmetic preparations for the skin including compositions and shaving aids to be used in conjunction with electric shavers.

U.S. Pat. No. 2,390,473 teaches a talcum powder stick to be applied prior to shaving with an electric shaver. Talc is formed into a stick that is coated with plastic to prevent crumbling. The talc may be scented.

U.S. Pat. No. 2,548,891 teaches a method of making a shaving aid, wherein talcum powder is mixed with molten wax and pressed into shaped pieces. This patent teaches that talc promotes sliding, thus making shaving easier especially with electric shavers. Talc is also useful in removing sweat.

U.S. Pat. No. 3,429,964 teaches a cosmetic composition in stick form used in electric dry shaving composition is said to improve lubrication of the skin at the same time removing moisture and perspiration and creating a sensation of smoothness of the skin surface. Mica is the primary ingredient. Also included are opacyifying agents such as zinc oxide and fillers such as gums which have incorporated therein other fillers such as kaolin and calcium carbonate as well as other materials such as zinc stearate. This composition can also be formed into a stick.

U.S. Pat. No. 4,457,912 teaches a method of shaving with an electric shaver using a pre-shave composition that comprises a lower alkyl alcohol and a quaternary cationic polymer. The polymer forms a stiff but pliable coating on each hair when the polymer dries. The polymer also neutralizes electric charges on the shaver so that the individual hairs are not repelled by the shaver when being cut. U.S. Pat. No. 4,933,177 is a cosmetic composition for the treatment of hair and skin. The composition is a powder with particle size lower than 125 microns. One of the ingredients is a plant having astringent properties such as acacia and a cohesion agent such as a solvent, a thickener or emulsifier. Example 25 shows a cheek make-up that includes talc, kaolin and zinc oxide.

U.S. Pat. No. 5,093,099 teaches a composition in the form of a flaky powder used as a medicine or cosmetic. The composition includes zinc oxide particles between 0.1 and 1 micron. While zinc oxide is the main ingredient, bases mixed therewith can include kaolin. Most of the preparations are either of an oily nature or creams and are not intended as pre-shaving preparations.

U.S. Pat. No. 5,165,915 teaches a cosmetic preparation in the form of a spherical clay powder that improves smoothness, slippage, and transparency. A composite powder can be applied as an aerosol spray using Freon.

The Formulary of Cosmetology teaches powders wherein dry skin must be covered with fatty powders and vice versa. A dry powder includes Magnesium Carbonate, colloidal kaolin and zinc oxide whereas a fatty powder includes zinc oxide, kaolin, calcium carbonate along with a metallic soap such as zinc stearate.

The prior art teaches that desirable attributes in a pre-shave composition preparatory to electric shaver use are ingredients that absorb oil, moisture, that act as lubricants, give a sense of smoothness and help neutralize static charges on the shaver. A number of preparations are also made in stick form and a perfume or scent is optionally provided.

While these preparations have been effective to some extent, a number of experiments have shown that the afore said compositions are not as effective as the composition of this invention. Either the compositions are deficient or lacking in the ingredients used in the invention or else the compositions include a multiple number of other ingredients which increase cost and are added in such proportions that the compositions did not achieve maximum effectiveness. While some cosmetic preparations do include the specific ingredients used in the composition of this invention, there is no indication that such cosmetics were contemplated to be used as a pre-shave composition. Besides, neither the granulometry nor the proportions of ingredients are the same or the equivalent of the composition of this invention.

It is an object of this invention to provide an electric shaver pre-shave composition that has but three ingredients in precise amounts.

It is a further object of this invention to provide an electric shaver pre-shave composition that has good absorbent qualities and also prevents clogging of the shaver blades.

It is still an object of this invention to provide a finely divided pre-shave electric shaver composition that can be dispensed as an aerosol spray, in a perforated container or packaged in vials having measured quantities.

This invention provides an electric shaver pre-shave composition that consists of only three ingredients and optionally a fragrant aroma and a flesh tint. The ingredients include an absorbent for oil in the skin, an absorbent for moisture that also provides a smooth gliding surface for the shaver as well as excellent adhesive qualities and a third ingredient which further enhances the absorbent qualities as well as prevents clogging of the shaver. It has been found that the most efficient method of application is to use an aerosol spray. By using this well known technique there is little waste or erratic spillage; however, the composition can also be dispensed from a perforated container that can be easily opened and manually applied.

The ingredients of the composition consist of:

| COMPONENT | PARTS BY WEIGHT |
| --- | --- |
| Kaolin (U.S.P.) | 20% |
| Zinc Oxide (U.S.P.) | 30% |
| Calcium Carbonate (U.S.P.) | 50% |

Kaolin absorbs excess oil on the skin. Zinc Oxide absorbs moisture, acts as a lubricant to provide a smooth gliding surface for the shaver and contributes adhesion quality. Calcium carbonate acts as a vehicle for the other ingredients, enhances the absorbent qualities of the other ingredients and provides the necessary lightness to prevent clogging of the shaver blades.

The above ingredients are blended together and triturated to a fine amorphous state wherein the particle size ranges from 50 to 100 microns, or wherein the majority of particles could pass through a 325 mesh screen. A small amount of fragrance or perfume and a flesh tint may also be added.

EXAMPLE 1

The following ingredients are blended together and placed in a dryer for 2 hours @350 F. Thereafter the blended, dried composition is pulverized in a Day triturator so that the blend will be ground to about 50–100 microns. The pulverized mixture is cooled and packaged in a perforated container.

EXAMPLE 1

The following ingredients are blended together and placed in a dryer for 2 hours @350° F. Thereafter the blended, dried composition is pulverized in a Day triturator so that the blend will be ground to about 50–100 microns. The pulverized mixture is cooled and packaged in a perforated container.

| INGREDIENT# | PARTS BY WEIGHT |
|---|---|
| Kaolin | 200 grams |
| Zinc Oxide | 300 grams |
| Calcium Carbonate | 500 grams |
| Aroma and Flesh Tint | 0–0.5% of total wght. |

U.S.P. Grade

EXAMPLE 2

The ingredients are prepared according to the procedure of Example 1 except that the drying time was 3 hours @300 F. and the compositoin was ground so that at least 90% of the powdered blend pased through a 325 mesh screen. The pulverized mixture was cooled and packed in an aerosol spray container. The aerosol was a compressed gas such as Nitrogen.

| Ingredient | Percentage by Weight |
|---|---|
| Kaolin | 20% |
| Zinc oxide | 30% |
| Calcium Carbonate | 50% |

EXAMPLE 3

The following ingredients were prepared according to the procedure of Example 1, except that the quantities used were larger.

| Ingredient | Parts by Weight |
|---|---|
| Kaolin | 1200 grams |
| Zinc Oxide | 1800 grams |
| Calcium Carbonate | 300 grams |

This composition was compared with some of the prior art products. For example, Zinc Oxide and Kaolin were used in the designated preparations and the only change was to substitute talc for the calcium carbonate maintaining the same proportions as in the invention. After talc, there were substituted corn starch and then sodium bicarbonate, again maintaining the same proportions as in the invention. All of these combinations proved totally unsatisfactory. The substituted composition would not remain on the skin for sufficient time to be effective as an absorbent, nor would the product form an effective gliding surface. The composition of this invention appears to have a synergistic effect that results in a superior product for its intended purpose.

While the preferred embodiments of the invention have been described herein, it is to be understood that various changes and modifications can be made without departing from the scope of the invention as defined by the appended claims.

What is claimed is:

1. An electric shaver dry pre-shave composition consisting of a finely ground blend of three ingredients in the prescribed proportions:

20% by weight of Kaolin,

30% by weight of zinc oxide,

50% by weight Calcium Carbonate, and said composition being ground to have a size range of 50 to 100 microns and said ingredients are of U.S.P. quality and up to 0.5% of the weight of said composition may include a perfume and a flesh tint.

2. A pre-shave composition as in claim 1 wherein said composition is dispensed from a perforated container.

3. The composition of claim 1 wherein said composition is finely ground to a size such that at least 90% will pass through a 325 mesh screen.

4. A pre-shave composition as in claim 1 wherein said Kaolin acts as an oil absorbent, said Zinc Oxide behaves as a moisture absorbent, a lubricant and as a skin adhesive and said Calcium carbonate serves as a vehicle for said Kaolin and Zinc Oxide, enhances the absorbent qualities and prevents clogging of the electric shaver.

5. A pre-shave composition of claim 4 wherein said composition is dispensed from an aerosol container wherein the propellent is a compressed gas.

* * * * *